United States Patent [19]

Potter

[11] Patent Number: 4,613,566

[45] Date of Patent: Sep. 23, 1986

[54] HYBRIDIZATION ASSAY AND KIT THEREFOR

[75] Inventor: Huntington Potter, Somerville, Mass.

[73] Assignee: President and Fellows of Harvard College, Cambridge, Mass.

[21] Appl. No.: 573,013

[22] Filed: Jan. 23, 1984

[51] Int. Cl.$^4$ .................. C12Q 1/68; G01N 33/566; G01N 33/567
[52] U.S. Cl. ........................... 435/6; 435/810; 436/501; 436/504; 436/808; 935/2; 935/77; 935/78
[58] Field of Search ............... 435/6, 91, 803, 810, 435/174, 179; 935/78, 77, 2; 436/63, 504, 501, 510, 518, 530, 808

[56] References Cited

U.S. PATENT DOCUMENTS

| | | | |
|---|---|---|---|
| 2,783,894 | 3/1957 | Lovell et al. | 210/500.2 |
| 3,876,738 | 4/1975 | Marinaccio et al. | 264/41 |
| 4,302,204 | 11/1981 | Wahl et al. | 935/78 X |
| 4,455,370 | 6/1984 | Bartelsman et al. | 935/78 X |
| 4,533,628 | 8/1985 | Maas | 435/6 |

OTHER PUBLICATIONS

Ranki et al., (1983), Gene 21: 77–85.
Masuda et al., (1979), Gene 6: 51–73.
Southern, J. Mol. Biol., vol. 98, 503–517, (1975).
Sato et al., PNAS, vol. 74, 542–546, (1977).
Wensink et al., Cell, vol. 18, 1231–46, (1979).

*Primary Examiner*—Sidney Marantz
*Assistant Examiner*—Cynthia L. Foulke

[57] ABSTRACT

A hybridization assay between two sets of parallel bands of DNA or RNA, one set labelled as a probe on a porous carrier sheet, the bands of the other set crossed with respect to the first and immobilized on a plurality of carrier sheets, is carried out with the sheets in contact and saturated with hybridization buffer in static condition. As many as ten sheets can be assayed simultaneously.

16 Claims, No Drawings

HYBRIDIZATION ASSAY AND KIT THEREFOR

The invention described herein was made with Federal Government support and the Government has certain rights in the invention.

This invention relates to an improved assay method utilizing DNA hybridization from porous carrier sheets and pertains more specifically to an improved assay method for enabling simple cross-hybridization of a labelled probe with multiple test specimens.

The Southern blot-hybridization procedure (Southern, J.Mol.Biol., Vol. 98, 503–517 (1975)) has been widely employed for detecting specific sequences among DNA fragments separated by gel electrophoresis. The procedure has been modified and extended to a so-called "two-dimensional" matrix of hybridization spots as described by Sato et al., PNAS, Vol. 74, 542–546 (1977); and by Wensink et al., Cell, Vol. 18, 1231–46 (1979). The modified procedure involves transferring a pattern of electrophoresed spaced bands of a DNA digest, each band containing separate DNA fragments from the electrophoresis gel to a porous carrier sheet and bonding or immobilizing it thereon by baking, then placing in face-to-face contact with a second gel containing a pattern of electrophoresed bands of a labelled DNA digest with the gel bands rotated approximately 90° with respect to the bands in the carrier sheet, then causing the labelled DNA fragments in the gel to flow through the carrier sheet, thus giving the fragments an opportunity to hybridize with the immobilized carrier sheet bands at the spots where the bands cross. Determining the location of labelled spots in the carrier sheet, for example by autoradiography or fluorography, makes it possible to determine which of the DNA fragments exhibit nucleotide sequences complementary to each band of the other pattern. This procedure makes it possible to determine in a single assay the complementarity of the DNA fragment in each gel band with that of each band in the carrier sheet.

However, the assay procedure is inefficient in that hybridization can occur only during the very brief time that any particular labelled fragment is actually traversing the carrier sheet containing the unlabelled DNA fragment. The inefficiency of this step requires that the radiolabelled DNA have a high specific activity, usually requiring that the DNA be nick-translated. This in turn leads to degradation of the DNA and consequent loss of resolution during gel electrophoresis and an additional loss of resolution resulting from flow of the hybridization buffer during the hybridization step.

The present invention provides a hybridization assay of such greatly improved resolution and sensitivity as to make possible simultaneous comparison of all fragments from as many as 10 different test specimens of DNA or RNA with all specimens of a DNA or RNA probe. The invention also enables the use of end-labelled DNA fragments when radiolabels are used, thus decreasing or eliminating degradation of the DNA caused by nick translation. The invention also features providing both the probe and test fragments of DNA or RNA in separate porous carrier sheets saturated with hybridization buffer and maintained in contact with each other while subjected to hybridization conditions. The invention also features maintaining the hybridization buffer in static condition during the hybridization step.

The invention is the method of assaying by hybridization a plurality of different DNA test fragments which comprises providing a probe sheet in the form of a pattern of parallel bands of labelled material comprising DNA or RNA fragments on a porous carrier sheet saturated with buffer free from solvent capable of eluting RNA or DNA from the probe sheet, providing a first test sheet comprising a pattern of parallel bands of test material comprising DNA or RNA fragments, unlabelled or bearing a label different from the probe fragments, immobilized on a porous carrier sheet saturated with hybridization buffer free from solvent capable of eluting RNA or DNA from the probe sheet, placing said first test sheet in face to face contact with said probe sheet with said probe and test bands crossing each other, providing at least one additional test sheet comprising a pattern of parallel bands of test material comprising DNA or RNA fragments, unlabelled or bearing a label different from the probe fragments, immobilized on a porous carrier sheet saturated with hybridization buffer containing solvent capable of eluting RNA or DNA from the probe sheet, at least one of said materials being DNA fragments, stacking said additional test sheets in face to face contact with said first test sheet at the side opposite said probe sheet with their bands aligned with the bands of said first test sheet to form an assemblage comprising said probe sheet and all said test sheets, subjecting said assemblage to hybridizing conditions while maintaining said hybridization buffer in static condition, separating said test sheets from said assemblage and washing to remove unhybridized labelled material therefrom, and determining on each test sheet the location of labelled material hybridized to said test material.

In a preferred embodiment, only the probe DNA or RNA fragments are labelled, for example radiolabelled, and the test material remains unlabelled. However, it is possible to practice the invention with labelled test material as well, provided the label of the test material is different from the label of the probe material, hence distinguishable from it, as in the case of tritium and $^{32}P$ labelling. It will also be appreciated that the invention can be practiced by providing simultaneously a second stack of test sheets on the opposite side of the probe sheet from the first stack. This procedure speeds up the procedure since the probe materials need diffuse only half as far to penetrate the same total number of test sheets as when the test sheets are all stacked on one side of the probe sheet.

The labelling employed may be radiolabelling, for example as pointed out above, or may be other forms of labelling embodying phosphorescence, chemiluminescence, biotin-avidin complexing, and the like, as is well known in the art.

While the parallel bands of DNA or RNA fragments, labelled or unlabelled, may be formed by any procedure, the invention is particularly applicable to assaying a pattern of parallel bands formed by gel electrophoresis of a DNA restriction digest or of RNA, the pattern being transferred from the gel to a porous carrier sheet by the Southern blot or by other conventional procedure such as electrophoresis. Any conventional porous carrier sheet for the DNA or RNA fragments may be employed in the practice of the present invention; among the materials adsorptive of nucleic acids which can be used are nitrocellulose paper, diazobenzyloxymethyl paper, and neutral or positively charged porous adsorptive nylon, i.e. any solid film-forming polyamide having an affinity for biological molecules. Such porous membranes are described in U.S. patents Lovell et al U.S. Pat. No. 2,783,894 and Marinaccio et al. U.S. Pat. No. 3,876,738. Porous carrier sheets of 66-nylon (copolymer of hexamethylene diamine and adipic acid) are available from several sources including AMF Inc., White Plains, N.Y., Pall Corp., Glen Cove, N.Y. Porous carrier sheets are also available from New England Nuclear Corp., Boston, Mass. under the trade names "GeneScreen" (neutral) and "GeneScreen Plus" (positively charged). The "GeneScreen Plus" porous carrier sheet can be used as the porous carrier sheet for the test sheets, but not for the probe sheet.

In the case of the probe sheet containing the bands of labelled probe material, the material is simply adsorbed on or in the sheet by transfer from the electrophoresis gel in which it is formed, without immobilization or bonding of the fragments to the carrier sheet but instead leaving the labelled material free to diffuse into contact with the bands of unlabelled material in the test sheets during the hybridization step. The test material in the test carrier sheets, on the other hand, is immobilized or bonded to the sheets by any conventional procedure such as baking at a temperature of 50°-100° C. In the case of "GeneScreen Plus" no baking is required, contact of the test material with the carrier sheet at room temperature sufficing to cause bonding; consequently this carrier sheet cannot be used for the probe sheet.

Physical movement or flow of the transfer or hybridization buffer during the hybridization step should be minimized or eliminated in order to provide high resolution and sensitivity of the assay; that is, the assemblage of probe sheet and test sheets is subjected to hybridizing conditions while maintaining the buffer in static condition. This can most conveniently be accomplished by confining the assemblage between rigid impervious parallel sheets such as glass sheets in contact with the outer sheets of the assemblage. In a preferred embodiment, an additional porous carrier sheet saturated with hybridization buffer containing solvent capable of eluting RNA or DNA from the probe sheet but free from either probe or test bands of material is interposed between the outermost test sheet and the rigid glass plate in order to enhance diffusion of the labelled material through the stack of test sheets and provide a small reservoir of hybridization buffer.

Any conventional buffers can be employed for the transfer buffer or the hybridization buffer, but it is essential that the buffer or buffers initially saturating the probe sheet and the first test sheet immediately in contact with the probe sheet be free from solvent capable of eluting DNA or RNA from the probe sheet. All of the remaining test sheets must be saturated with a hybridization buffer which does contain solvent capable of eluting DNA or RNA from the probe sheet. There may be used as the eluting solvent such materials as formaldehyde or formamide, the latter being preferred. Neither the eluting solvent nor the buffers is capable of eluting DNA or RNA from the test sheets on which it is immobilized. While the precise amount of such eluting solvent in the buffer is not critical, it is desirable that it amount to 30 to 60% by weight of the total buffer. The remainder of the buffer, as well as the transfer buffer free from eluting solvent, may be of conventional composition; preferably the buffer contains sodium dodecyl sulfate (SDS) as a wetting agent. The length of time required for complete diffusion equilibration of the buffers to occur, which is desirable for best results, varies depending upon temperature and the total number of carrier sheets (as well as their thickness and porosity) in the stack or stacks. Although a temperature as low as about 30° C. can be used for hybridization in some cases, in order to ensure completion of the hybridization step it is preferred to heat the assemblage to a temperature of about 80°-100° C. and also to incubate it for a few hours at a temperature from room temperature to 42° C.

The present invention is particularly adapted for restriction mapping of a genome. In using it for this purpose, the sizes of the various DNA fragments generated by the desired number of different restriction enzymes is first determined, for example, by gel electrophoresis using known standards.

One of the digests is then selected for labelling, e.g. end-labelling with $^{32}P$ to serve as the probe. Preferably, the digest serving as a probe should contain a greater than average number of fragments and should contain no fragments that are so similar in size that they cannot be resolved by electrophoresis.

The desired map can be deduced by identifying and tabulating the particular fragments from each test sheet digest which hybridize with each fragment of the labelled probe sheet digest.

A kit for practicing the method of the invention includes a supply of porous carrier probe sheets and test sheets, a supply of buffer free from solvent capable of eluting DNA or RNA from a probe sheet, a supply of buffer containing a solvent capable of eluting DNA or RNA from a probe sheet, and optionally means for maintaining a probe sheet and at least one test sheet saturated with said buffers in static condition, and, if desired, a supply of labelled DNA or RNA fragments, and a supply of templates for cutting and pasting a restriction map. The means for maintaining the carrier sheets saturated with buffers under static condition, as described more fully in the Example which follows, may include tray, roller, glass or other impervious plates, and clamps.

The following specific example will serve as an illustration of the present invention without acting as a limitation upon its scope.

EXAMPLE

Several-microgram aliquots of adenovirus DNA were digested with the four restriction enzymes HindIII, EcoR1, BamH1 and Kpn1. A small portion of one digest (HindIII) was end-labelled with $^{32}P$ nucleotides using the Klenow fragment of DNA polymerase I. (Alternatively, the fragments may be labelled using polynucleotide kinase or by allowing the T4 DNA polymerase to act first as a 3′ 5′ exonuclease in the absence of DNA precursors and then as a polymerase in the presence of $^{32}P$ dXTPs).

A few $\mu g$ of DNA from each non-radioactive digest were then subjected to electrophoresis in a separate agarose gel (1% agarose in 40 mM Tris, 20 mM Na-Acetate, 1 mM EDTA, pH 7.5) by loading in a single 15 cm wide well. Electrophoresis was performed for a time compatible with having the fragments well separated with the smallest one no more than about 14 cm from the origin and at a low enough voltage (2 v/cm) so that the bands were sharp and undistorted across the width of the gel. The gels were stained with ethidium bromide and photographed with a ruler alongside to record the positions of the bands. Each gel was trimmed into a square 15 cm on a side with one corner (the bottom left) cut off at an angle for orientation purposes.

(For the procedures that follow, the gel was never turned over so that orientation would not become confused.)

Each gel was then treated as for a Southern blot—denatured with 0.5M NaOH, 1M NaCl, neutralized with a buffer consisting of 1M Tris-HCl pH 7.5, 1M NaCl followed by 25 mM sodium phosphate, pH 6.5 and transferred to 15 cm. square nitrocellulose filter paper or preferably, to GeneScreen as a carrier sheet. The great advantages of "GeneScreen" are that it binds more quantitatively than nitrocellulose, especially the short DNA fragments, is much less subject to tearing and breaking, and does not permanently stick together in the sandwich. The orientation of the gel on the carrier sheet was marked on a corner of the sheet before transfer. Following the transfer, the carrier sheets were washed briefly in transfer buffer (25 mM sodium phosphate, pH 6.5) and vacuum-baked at 80° C. for 2–3 hr. to immobilize the unlabelled DNA bands on the sheet, forming test sheets.

The $^{32}P$ labelled DNA was subjected to similar electrophoresis using the 15 cm wide loading well. Again the gel was trimmed, a corner was cut off and the gel was prepared and blotted onto carrier sheet in the same manner as were the gels of the cold digests except that the baking step was omitted.

Several hours (or more, if desired) before the transfer of the labelled DNA was complete, one of the test sheets was soaked in degassed non-formamide hybridization buffer (5×SSC [SSC=0.15 M NaCl, 0.015 M Na-citrate], 25 mM sodium phosphate, pH 6.5, 10×Denhardt's solution [Denhardt's=0.02% Bovine serum albumin; 0.02% Ficoll 400; 0.02% polyvinyl pyrollidone], 0.1% SDS, 0.1% Na pyrophosphate, 200 μg/ml denatured non-homologous DNA) at 65° C. The other test sheets were soaked in degassed formamide hybridization buffer (5×SSC, 25 mM sodium phosphate, pH 6.5, 10×Denhardt's solution, 0.1% SDS, 0.1% Na pyrophosphate, 200 μg/ml denatured non-homologous DNA, 50% formamide).

The hybridization sandwich or stack could now be constructed. One clean, glass electrophoresis plate (20 cm×20 cm×4 mm) was placed flat on a sturdy surface such that the plate extended about 3 cm beyond the support on both the left and right sides. The probe sheet was removed from the transfer apparatus and rinsed in 25 mM sodium phosphate, pH 6.5 and placed on the gel plate. The surface of the paper adjacent to the gel during transfer was "face up" and the paper was oriented so that the high molecular weight DNA species were on the left side, and the low MW species on the right. Care was taken not to trap bubbles between the glass plate and the paper. A hard rubber artist's roller was used to roll the paper flat and expel air bubbles (rolling from front to back).

Next the test sheet in non-formamide hybridization buffer was laid face down exactly on top of the probe sheet but turned 90° with respect to the orientation of the probe sheet (with the large fragments toward the far edge), and air bubbles eliminated. Each band of DNA on the test sheet thus intersected each band on the probe sheet at right angles. The sheets were carefully rolled together with the artist's roller from front to back. Then one by one the other test sheets were laid down on top of the growing stack with their bands aligned with (parallel to) those of the first test sheet, being careful not to trap air bubbles between the sheets. When the stack was complete, the sheets were again rolled tightly together with the artist's roller from front to back. Most of the hybridization buffer was extruded from between the papers. Finally, a 15×15 cm piece of 0.33 MM thick cellulose chromatography paper (Whatman 3 MM paper) was soaked in the remaining formamide hybridization buffer and laid on top of the stack and rolled again. More formamide hybridization buffer containing formamide was poured on the top (3 MM) sheet, especially at the near edge. Then the edge of a second 20 cm×20 cm glass plate was placed along the near edge of the first plate and tilted down and away until the stack of sheets was sandwiched between the two glass plates. The plates were clamped together on the two sides. It was important that the pressure of the clamps be over the part of the plates under which the papers extend and that the sandwich be kept horizontal to minimize or eliminate further flow of the buffer.

Alternatively, a length of compressible rubber tubing can be placed between the plates around three sides of the stack of papers to act as a liquid seal, permitting the assemblage to be positioned vertically with the unsealed fourth side facing up to allow bubbles to escape during the subsequent heating step.

The hybridization cell or assemblage was incubated at room temperature one to two hours to allow the hybridization solutions to equilibrate, then placed in a 100°–110° C. oven until the hybridization buffer just began to boil or until a surface thermometer read 100°–110° C. Alternatively, heating to 80° C. is usually sufficient. Finally, the assemblage was incubated at 37°–42° C. overnight to complete the hybridization.

Following the hybridization, the glass plates were pried apart and the test sheets washed three times for 20 minutes each at 20° C. in 2×SSC, 0.1% SDS, then twice for 40 min. at 50° C. in 0.1×SSC, 0.1% SDS. The test sheets were dried and autoradiographed all in the same orientation (which was carefully noted). The 3 MM paper and the original $^{32}P$ labelled DNA probe sheet were placed in waterproof plastic envelopes and an autoradiogram of each was obtained to indicate the positions of the labelled DNA bands and the extent of transfer of labelled DNA through the stack of recipient blots and thus to serve as a guide in determining locations.

The information in the autoradiogram of the test sheets consists of spots of hybridization at the intersection of $^{32}P$ DNA bands with non-radioactive DNA bands that contain complementary sequences. The restriction map can be directly deduced from the positions of the hybridization spots. A labelled fragment is arbitrarily chosen as a starting place and the unlabelled fragments of a given digest that hybridize to that labelled fragment are placed adjacent to each other. The other labelled fragments that hybridize to these unlabelled fragments are then placed on the map appropriately next to the *first* labelled fragment. Thus one can "walk" in both directions down the DNA molecule, "stepping" first on a labelled fragment then on an unlabelled, then on a labelled, etc. Of course, if an unlabelled fragment is contained entirely within a labelled fragment, there will be only a *single* hybridization spot for that unlabelled fragment, but this does not interrupt the walk. The same procedure is then repeated, comparing each of the unlabelled digests to the labelled digest until all unlabelled digests have been mapped with respect to the labelled digest and thus to each other. Ambiguities in a single labelled-unlabelled comparison are almost always resolved by the time all unlabelled digests are mapped.

Labelled and/or unlabelled RNA can be substituted for the labelled and/or unlabelled DNA in the foregoing procedure without change except that in transferring the RNA to a porous sheet the steps of denaturing with NaOH and NaCl, neutralizing with Tris buffer, and with sodium phosphate buffer are omitted and the RNA is transferred directly, as is well known in the art.

What is claimed is:

1. The method of assaying by hybridization a plurality of DNA or RNA fragments which comprises
    providing a probe sheet in the form of a pattern of parallel bands of labelled probe material comprising DNA or RNA fragments on a porous carrier sheet saturated with buffer free from solvent capable of eluting DNA or RNA fragments from said probe sheet,
    providing a first test sheet comprising a pattern of parallel bands of test material comprising DNA or RNA fragments, unlabelled or labelled differently from said probe material, said test material being immobilized on a porous carrier sheet saturated with buffer free from solvent capable of eluting DNA or RNA fragments from said probe sheet,
    placing said first test sheet in face to face contact with said probe sheet with said patterns of bands rotated with respect to each other so that said bands cross each other,
    providing at least one additional test sheet comprising a pattern of parallel bands of test material comprising DNA or RNA fragments immobilized on a porous carrier sheet saturated with buffer containing solvent capable of eluting DNA or RNA fragments from said probe sheet,
    stacking said additional test sheets in face to face contact with said first test sheet at the side opposite said probe sheet with their bands aligned with the bands of said first test sheet to form an assemblage comprising said probe sheet and all said test sheets,
    maintaining said assemblage at a temperature from 30° to 100° C. to permit hybridization to occur while maintaining said buffers in static condition,
    separating said test sheets from said assemblage and washing to remove unhybridized labelled material therefrom, and
    determining on each test sheet the location of hybridized material.

2. The method as claimed in claim 1 in which said solvent is formamide or formaldehyde.

3. The method as claimed in claim 1 in which said probe material is radiolabelled and said test material is unlabelled and said solvent is formamide.

4. The method as claimed in claim 3 in which at least one said pattern of parallel bands is formed by gel electrophoresis of a DNA restriction digest and transfer of the resulting pattern to said porous carrier sheet.

5. The method as claimed in claim 3 in which said labelled DNA fragments are end-labelled.

6. The method as claimed in claim 3 in which said test material is immobilized on said porous carrier sheets by baking at 50°–100° C.

7. The meth as claimed in claim 1 in which said probe material is radiolabelled and the location of said labelled hybridized material on said test sheets is determined by autoradiography.

8. The method as claimed in claim 1 including the step of confining said assemblage between rigid impervious parallel sheets while subjecting said assemblage to hybridization conditions.

9. The method as claimed in claim 1 in which said porous carrier sheets comprise nitrocellulose paper.

10. The method as claimed in claim 1 in which all said patterns of parallel bands are formed by gel electrophoresis of a DNA restriction digest and transfer of the resulting pattern from said gel to said porous carrier sheet, said labelled probe framents are end labelled by radiolabeling, said test material is unlabelled, and said assemblage is confined between rigid impervious parallel sheets while maintained at a temperature from 30° to 100° C. to permit hybridization to occur.

11. The method as claimed in claim 10 in which said solvent is formamide or formaldehyde and said porous carrier sheets comprise nylon 66.

12. The method as claimed in claim 11 in which said solvent is formamide.

13. The method as claimed in claim 12 in which the location of said labelled hybridized material on the test sheets is determined by autoradiography.

14. A kit for hybridization assay of a plurality of DNA or RNA fragments which comprises
    a supply of porous carrier probe sheets and porous test sheets,
    a supply of buffer free from solvent capable of eluting DNA or RNA fragments from a probe sheet, and
    a supply of buffer containing a solvent capable of eluting DNA or RNA from a probe sheet.

15. A kit as claimed in claim 14 which comprises in addition means for maintaining a probe sheet and at least one test sheet saturated with said buffers in static condition.

16. A kit as claimed in claim 15 which comprises in addition a supply of labelled DNA or RNA fragments suitable for use as probe material.

* * * * *